(12) United States Patent
Enomoto

(10) Patent No.: US 7,769,433 B2
(45) Date of Patent: Aug. 3, 2010

(54) LIGHT SOURCE APPARATUS FOR ENDOSCOPE

(75) Inventor: Takayuki Enomoto, Saitama (JP)

(73) Assignee: Hoya Corporation, Tokyo (JP)

( * ) Notice: Subject to any disclaimer, the term of this patent is extended or adjusted under 35 U.S.C. 154(b) by 826 days.

(21) Appl. No.: 11/552,730

(22) Filed: Oct. 25, 2006

(65) Prior Publication Data

US 2007/0093688 A1    Apr. 26, 2007

(30) Foreign Application Priority Data

Oct. 26, 2005  (JP) .......................... P2005-311685

(51) Int. Cl.
*A61B 5/055* (2006.01)
(52) U.S. Cl. ...................... 600/476; 600/178
(58) Field of Classification Search ................. 600/178, 600/180, 181, 160, 101; 362/553, 554, 572, 362/574; 372/29.01, 29.011, 38.01, 38.03, 372/38.09; 606/11, 12
See application file for complete search history.

(56) References Cited

U.S. PATENT DOCUMENTS

| 4,070,681 | A | * | 1/1978 | Ichikawa et al. | ............ 347/255 |
|---|---|---|---|---|---|
| 4,994,675 | A | * | 2/1991 | Levin et al. | .................. 250/551 |
| 5,971,978 | A | * | 10/1999 | Mukai | .......................... 606/18 |
| 6,468,204 | B2 | | 10/2002 | Sendai et al. | |
| 6,663,561 | B2 | * | 12/2003 | Sugimoto et al. | ........... 600/160 |
| 7,037,259 | B2 | * | 5/2006 | Hakamata et al. | ........... 600/178 |
| 2002/0136248 | A1 | * | 9/2002 | Minneman | .................... 372/28 |
| 2003/0020888 | A1 | * | 1/2003 | Tanaka et al. | ................. 355/30 |

* cited by examiner

*Primary Examiner*—Long V Le
*Assistant Examiner*—Nicholas L Evoy
(74) *Attorney, Agent, or Firm*—Greenblum & Bernstein, P.L.C.

(57) ABSTRACT

A light source apparatus for an endoscope includes an exciting laser light source, a monitor sensor, an indicator, a shutter mechanism, an optical system, and a controller. The controller intermittently turns on the exciting laser light source for testing and controls the shutter mechanism so as to close the optical path of the exciting light, during a period after laser irradiation is permitted until the monitor sensor outputs the turn-on enable signal. The controller controls the shutter mechanism so as to open the optical path of the exciting light and controls the indicator so as to indicate to the effect that the exciting laser light source is ready for immediate emission, when the monitor sensor outputs the turn-on enable signal. Further, the controller turns on the exciting laser light source when an exciting light turn-on signal is input, thereby making the exciting light incident upon the light guide.

2 Claims, 7 Drawing Sheets

LIGHT SOURCE APPARATUS FOR ENDOSCOPE

BACKGROUND OF THE INVENTION

The present invention relates to a light source apparatus for an endoscope that makes an exciting light for fluorescence excitation incident upon a light guide in an endoscope.

An organism tissue is excited and generates fluorescence when irradiated with a light of a specific wavelength. An abnormal organism tissue suffering a lesion such as a tumor or cancer generates weaker fluorescence than a normal organism tissue. Such reaction is also seen in an organism tissue under a body cavity wall. Recently, endoscope systems that detect a lesion that has emerged in an organism tissue under a body cavity wall based on such reaction have been developed.

One of such endoscope systems is designed to perform a normal observation mode of emitting an illuminating light of a visible wavelength range from a tip portion of the endoscope to illuminate inside of the body cavity and shooting an image formed by the illuminating light reflected by a surface of the body cavity wall with an imaging apparatus, as well as a fluorescence observation mode of emitting a light of a specific wavelength range from the tip portion of the endoscope for exciting the organism tissue, and shooting an image formed by the fluorescence generated by the organism tissue excited by such light under the body cavity, with the imaging apparatus.

A light source apparatus employed in the endoscope system described above includes therein a visible light source and an exciting light source, and an optical path merging device such as a dichroic mirror that merges an optical path of the illuminating light emitted by the visible light source and that of the exciting light emitted by the exciting light source. The light source apparatus provides to a light guide fiber bundle of the endoscope connected to the light source apparatus, the illuminating light emitted by the visible light source in the normal observation mode, and the exciting light emitted by the exciting light source in the fluorescence observation mode.

Conventionally a mercury vapor lamp or a xenon lamp has been employed as the light source of the exciting light. The mercury vapor lamp, however, cannot be instantaneously turned on and off, which disturbs quick switching with the illuminating light, and besides turns into a hazardous waste when disposed. Also, the visible light emitted by the xenon lamp is not capable of sufficiently exciting the organism tissue, and hence a photomultiplier tube has to be employed for capturing the dim fluorescence, which makes the imaging apparatus more complicated.

Accordingly, the light source apparatus for an endoscope lately developed employs, as disclosed in U.S. Pat. No. 6,468, 204, for example, an UV-emitting type semiconductor laser as the exciting light source. Employing such semiconductor laser allows instantaneously turning on and off, and also creating the fluorescence having sufficient intensity.

When employing the laser light source as the exciting light source, however, a certain preparation period (approx. three minutes in case of the semiconductor laser) is required before the laser beam becomes ready to be stably output, upon turning on the power for the light source apparatus to activate the laser light source by cold boot. Therefore the operator has to take the trouble to press the turn-on button several times, before the laser beam is stably output.

In view of the foregoing problems incidental to the conventional art, aspects of the invention is advantageous in that, there is provided a light source apparatus for an endoscope capable of quickly starting to stably output an exciting light without the need to repeatedly press the turn-on button after turning on the power, even when a laser light source is employed as the exciting light source.

Aspects of the invention provided a light source apparatus for an endoscope, designed to make an exciting light that excites an organism tissue to thereby induce fluorescence incident upon a light guide disposed through a portion of the endoscope to be inserted into a body cavity, comprising an exciting laser light source that emits the exciting light; a monitor sensor that monitors an output of the exciting laser light source and outputs a turn-on enable signal when the exciting laser light source is ready to stably emit a beam; an indicator that indicates whether the exciting laser light source is ready for immediate emission; a shutter mechanism that opens and closes an optical path of the exciting light; an optical system that makes the exciting light that has passed the shutter mechanism incident upon a proximal facet of the light guide; and a controller that controls the exciting laser light source. The controller intermittently turns on the exciting laser light source for testing and controls the shutter mechanism so as to close the optical path of the exciting light, during a period after laser irradiation is permitted until the monitor sensor outputs the turn-on enable signal; controls the shutter mechanism so as to open the optical path of the exciting light and controls the indicator so as to indicate to the effect that the exciting laser light source is ready for immediate emission, when the monitor sensor outputs the turn-on enable signal; and turns on the exciting laser light source when an exciting light turn-on signal is input, thereby making the exciting light incident upon the light guide.

It is preferable that the controller controls the indicator, after the laser irradiation is permitted and before the monitor sensor outputs the turn-on enable signal so as to indicate to the effect that the exciting laser light source is in a preparation phase for emission.

BRIEF DESCRIPTION OF THE ACCOMPANYING DRAWINGS

DETAILED DESCRIPTION OF THE EMBODIMENT

Figure 1:
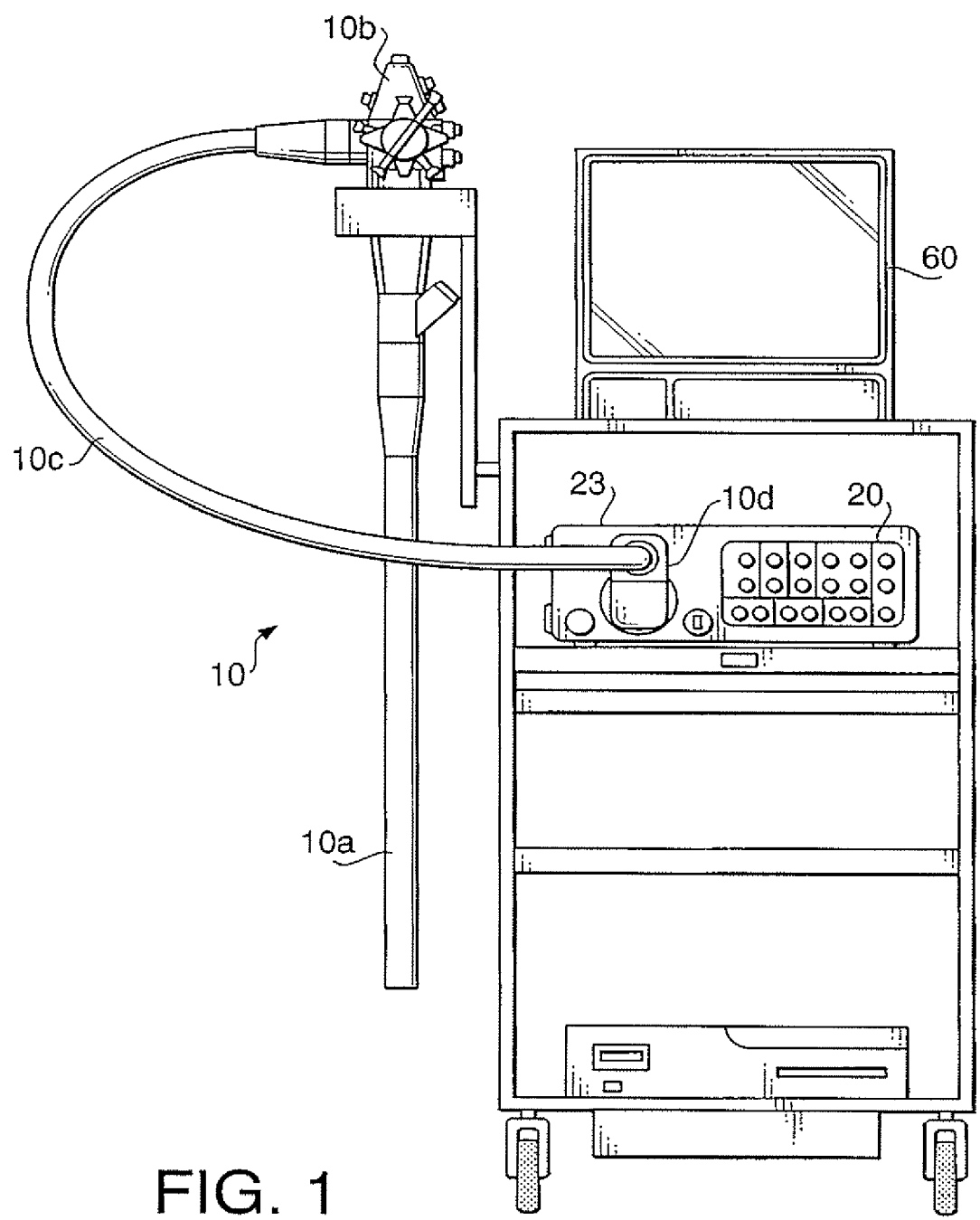
FIG. 1 is a drawing illustrating an appearance of a fluorescence endoscope system including a light source apparatus for an endoscope according to an embodiment of the present invention.
Figure 2:
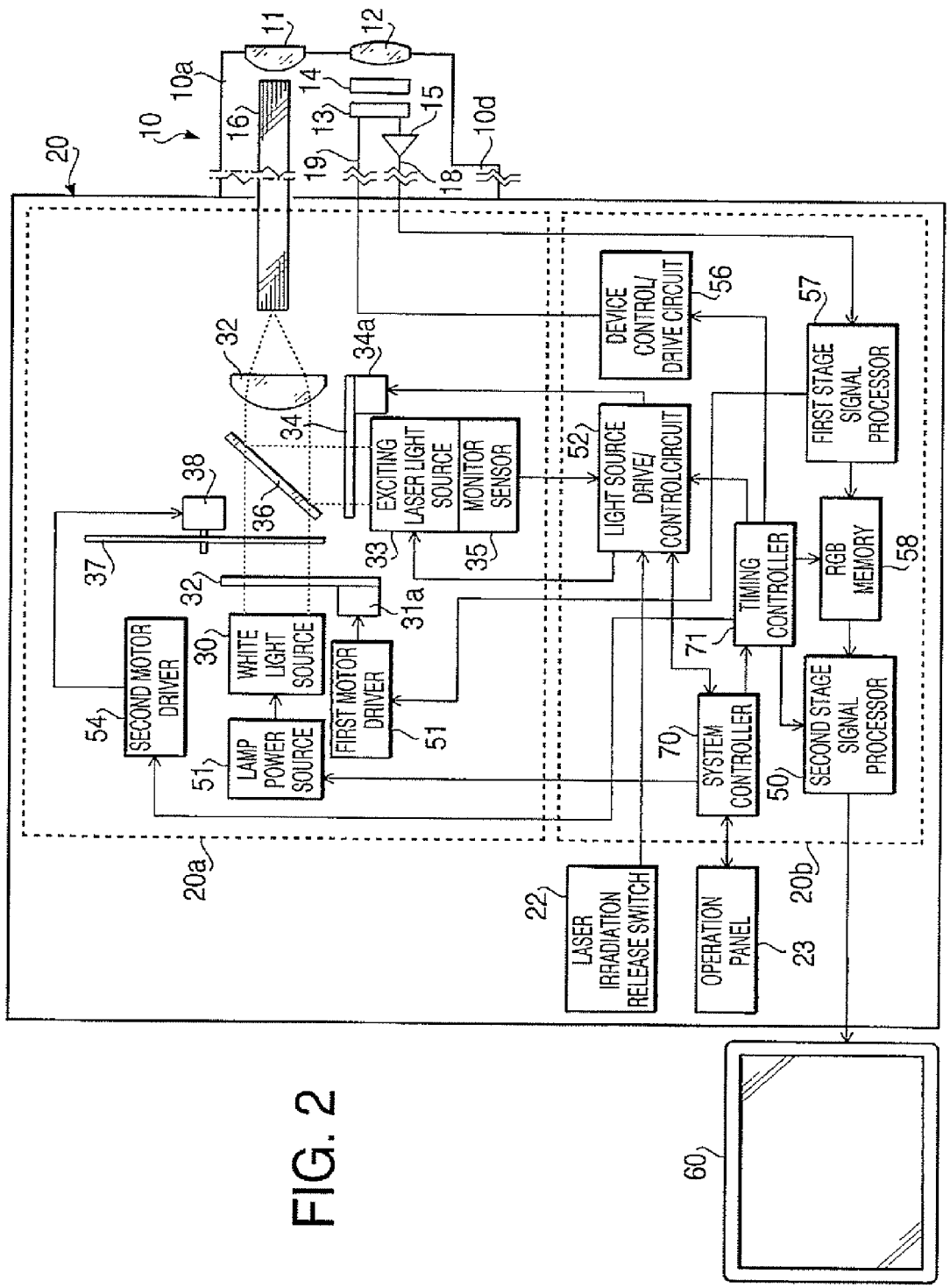
FIG. 2 is a block diagram showing an internal configuration of the fluorescence endoscope system shown in FIG. 1.

Hereunder, an embodiment of the present invention will be described referring to the accompanying drawings. FIG. 1 is a drawing illustrating an appearance of a fluorescence endoscope system including a light source apparatus for an endoscope according to the embodiment of the present invention, and FIG. 2 is a block diagram showing an internal configuration of the fluorescence endoscope system.

As shown in FIG. 1 the fluorescence endoscope system includes a fluorescence observation endoscope 10, a light source processing apparatus 20 capable of acting as a light source apparatus for an endoscope, and a monitor 60.

The fluorescence observation endoscope 10 is constituted of an ordinary electronic endoscope into which a modification for the fluorescence observation is incorporated, and includes an insertion tube 10a formed in a slender shape to be inserted into a body cavity and including at its tip portion a bendable portion that can be bent, an operating unit 10b including an angle knob for manipulating the bendable portion of the insertion tube 10a, a light guide flexible tube 10c for connecting the operating unit 10b and the light source apparatus 20, and a connector 10d provided at an proximal end portion of the light guide flexible tube 10c.

The light source processing apparatus 20 is provided with a laser irradiation release switch 22, serving as a safety device for preventing untimely emission of the laser employed as the exciting light, and an operation panel 23, on the front face thereof. The details of the operation panel 23 will be subsequently described.

Referring to FIG. 2, detailed configuration of the fluorescence observation endoscope 10 and the light source processing apparatus 20 according to the embodiment will be described by turns. The insertion tube 10a of the fluorescence observation endoscope 10 is provided with a distributor lens 11 and an objective lens 12 at a distal tip portion thereof. Incorporated inside the distal tip portion of the insertion tube 10a are an imaging device 13 capable of shooting a color image, such as a CCD color image sensor that shoots an image of an object formed by the objective lens 12, an exciting light cut filter 14 that eliminates a wavelength component corresponding to a laser beam for fluorescence excitation, to be described later, from a light emitted through the objective lens 12 and returning to the imaging device 13, and a cable driver 15 that amplifies an image signal output by the imaging device 13.

The exciting light cut filter 14 has a characteristic of blocking the exciting light but transmitting a light of a longer wavelength than the exciting light, so as to prevent the exciting light from being incident upon the imaging device 13 during fluorescence imaging, thereby enabling shooting the image exclusively based on autofluorescence. It is to be noted that a light of a near-UV wavelength range that induces the autofluorescence is selected as the exciting light, and therefore cutting off the exciting light component by the exciting light cut filter 14 does not affect the imaging performance of the Blue component when shooting an ordinary color image.

To transmit the image signal driven by the cable driver 15, an image signal cable 18 is inserted through inside the insertion tube 10a, the operating unit 10b and the light guide flexible tube 10c, and connected to a circuit to be described later, in the light source processing apparatus 20 connected to the fluorescence observation endoscope 10.

Parallel to the signal cable 18, a light guide 16 constituted of a bundle of a plurality of optical fibers and a drive signal cable 19 that provides a drive signal to the imaging device 13 are inserted through the insertion tube 10a, operating unit 10b and the light guide flexible tube 10c. An end portion of the light guide 16 opposes the distributor lens 11 inside the distal tip portion of the insertion tube 10a, and a proximal end portion thereof is inserted into and fixed to the light source processing apparatus 20.

The light source processing apparatus 20 is divided into two blocks, namely a light source block 20a that selectively provides a white light for observation of an internal portion of the body cavity and the exciting light that excites an organism tissue on the body cavity wall so as to induce the autofluorescence, to a proximal facet of the light guide 16 in the fluorescence observation endoscope 10, and an image-processing block 20b that processes the image signal received from the cable driver 15 in the fluorescence observation endoscope 10 to thereby generate a picture signal, and outputs the picture signal to the monitor 60.

The optical system provided in the light source block 20a of the light source processing apparatus 20 includes a white light source 30 that emits a generally parallel visible light (white light), a light control diaphragm 31 that adjusts the optical flux diameter of the white light emitted by the white light source 30, and a condenser lens 32 that collects the white light that has passed through the light control diaphragm 31 and makes the white light incident upon the proximal facet of the light guide 16, as well as an exciting laser light source 33 that emits a generally parallel exciting light, and a dichroic mirror 36 that merges the optical path of the exciting light emitted by the exciting laser light source 33 and that of the white light. Also, though not shown, the white light source 30 includes a lamp and a reflector, and the exciting laser light source 33 includes a semiconductor laser that emits a divergent light and a collimator lens that converts the divergent light into a parallel light, The light control diaphragm 31 is driven by a diaphragm motor 31a so as to adjust the amount of the white light. The optical path from the white light source 30 to the light guide 16 is linear, and the optical path of the exciting light orthogonally intersecting with such optical path is merged therewith by the dichroic mirror 36 acting as an optical path merging device. The dichroic mirror 36 is inclined by 45 degrees with respect to the optical axis of the condenser lens 32, and serves to transmit the visible light, to reflect a light of a near-UV wavelength range, and to lead the transmitted white light and the reflected near-UV light serving as the exciting light to a single optical path directed to the proximal facet of the light guide 16. The dichroic mirror 36 and the condenser lens 32 correspond to the optical system which makes the exciting light incident upon the proximal face of the light guide 16 in the endoscope.

Figure 3:
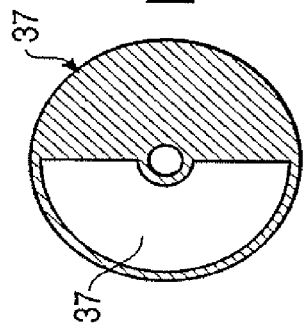
FIG. 3 is a plan view showing a rotary shutter employed in the light source processing apparatus shown in FIG. 1.

Between the white light source 30 and the dichroic mirror 36, a rotary shutter 37 is disposed so as to intermittently turn on and off (transmit or block) the white light. The rotary shutter 37 is, as shown in a plan view in FIG. 3, constituted of a circular disk with a sector-shaped window 37a having a central angle of approx. 180 degrees, and is fixed to a tip portion of the rotating shaft of the shutter motor 38 in an orientation orthogonal to the optical axis of the condenser lens 32 and in an offset state. The size of the window 37a is set larger than the diameter of the white light, so that when the shutter motor 38 is driven so as to rotate the rotary shutter 37 the white light is turned on and off, thus to be intermittently transmitted.

Between the exciting laser light source 33 and the dichroic mirror 36, an exciting light shutter 34 is disposed so as to open and close the optical path of the exciting light. The exciting light shutter 34 is driven by a solenoid 34a, and serves to block the optical path of the exciting light thus to keep the laser beam from being unduly emitted outward, when the light source processing apparatus 20 performs the test emission as will be subsequently described. The exciting light shutter 34 and the solenoid 34a serve to perform as the shutter mechanism which opens and closes the optical path of the exciting light.

The light source block 20a of the light source processing apparatus 20 further includes a monitor sensor 35 that monitors the output of the exciting laser light source 33 and outputs a status signal, a lamp power source 51 that supplies power to the white light source 30, a first motor driver 53 that drives the diaphragm motor 31a, and a second motor driver 54 that drives the shutter motor 38. Here, the monitor sensor 35 outputs an emission enable signal as the status signal when the exciting laser light source 33 can stably emit a beam, and outputs an emission disable signal in other occasions.

On the other hand, the image-processing block 20b in the light source processing apparatus 20 includes an exciting light source drive/control circuit 52 that drives the exciting laser light source 33 for turning it on and off and also drives the solenoid 34a so as to open and close the exciting light shutter 34 according to the status signal output by the monitor sensor 35, and an imaging device control/drive circuit 56 that drives the imaging device 13. The image-processing block 20b also includes, as an image signal processing system, a first stage signal processor 57 that processes the image signal received from the cable driver 15, a RGB memory 58 that temporarily stores a digital image signal processed and output by the first stage signal processor 57, and a second stage signal processor 59 that converts the digital image signal read out from the RGB memory 58 into a standardized picture signal to be displayed on the monitor and outputs such signal, as well as a system controller 70 and a timing controller 71 that control an entirety of the foregoing components.

The system controller 70 is electrically connected to various switches and indicators arranged on the operation panel 23, for controlling the lamp power source 51 and the exciting light source drive/control circuit 52 based on the setting of the switches so as to continuously turn on and off the white light and the exciting light, and to switch the display on the monitor 60.

Figure 4:
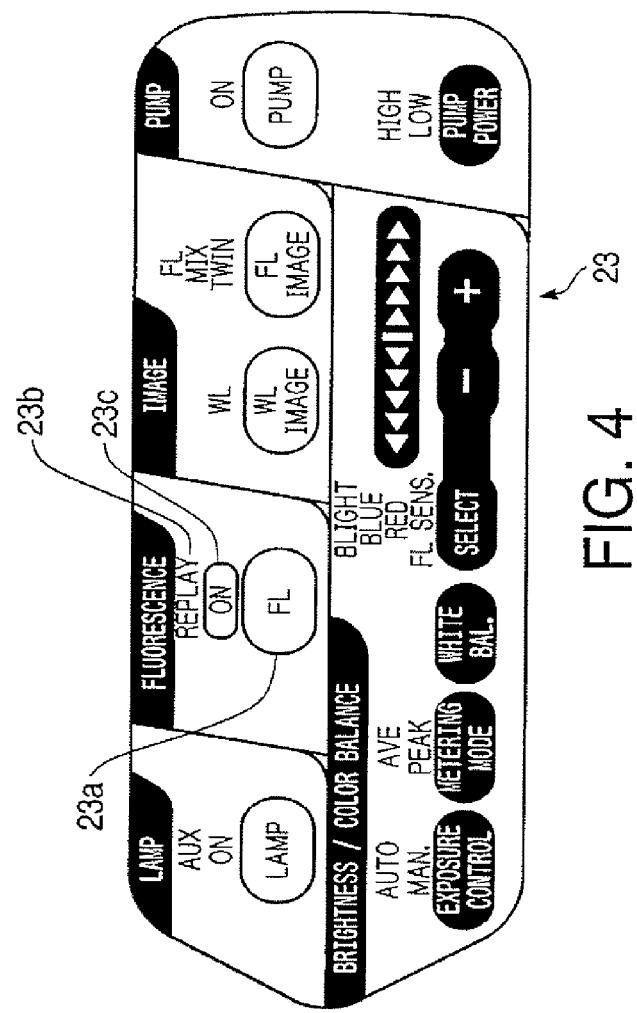
FIG. 4 is a plan view showing an operation panel provided in the light source processing apparatus shown in FIG. 1.

The operation panel 23 includes, as shown in FIG. 4, various operating switches and indicators that indicate the state of the light source processing apparatus 20. Among those switches and indicators, the ones related to the present invention include a laser turn-on button 23a denoted by a code FL, a laser status indicator 23b denoted by a code "READY", and a laser output indicator 23c denoted by a code "ON". The laser status indicator 23b serves as the indicator that indicates whether the exciting laser light source is ready for immediate emission, and is turned on when the exciting laser light source 33 is ready for immediate emission according to a signal from the system controller 70; blinks during the test emission of the laser light source in a preparation phase; and is turned off when the power for the apparatus is disconnected. The laser output indicator 23c is turned on when the exciting laser light source 33 is turned on and the exciting light is being emitted to the light guide 16, and otherwise turned off, according to a signal from the system controller 70.

The timing controller 71 controls, according to the instruction from the system controller 70, the exciting light source drive/control circuit 52 so as to intermittently turn on and off the exciting light at a predetermined timing, and also controls the second motor driver 54 that drives the shutter motor 38 so as to intermittently turn on and off the white light at a predetermined timing. The timing controller 71 also controls the shooting timing of the imaging device 13 via the imaging device control/drive circuit 56, and controls, in synchronicity therewith, writing and reading of data in and out of the RGB memory 58 (address data control), and also instructs a processing timing of the image signal to the second stage signal processor 59.

In this embodiment, the exciting light source drive/control circuit 52 performs as the controller that controls the exciting laser light source 33. To be more detailed, the exciting light source drive/control circuit 52 intermittently turns on the exciting laser light source 33 for testing during the period after the laser irradiation release switch 22 is turned on and the laser irradiation is permitted until the monitor sensor 35 outputs the turn-on enable signal, and controls the solenoid 34a so as to close the exciting light shutter 34 thus to close the optical path of the exciting light, and to open the exciting light shutter 34 thus to open the optical path of the exciting light once the monitor sensor 35 outputs the turn-on enable signal.

The exciting light source drive/control circuit 52 also controls, during the period after the laser irradiation release switch 22 is turned on and the laser irradiation is permitted until the monitor sensor 35 outputs the turn-on enable signal, the system controller 70 so as to cause the laser status indicator 23b on the operation panel 23 to blink and thus to indicate that the exciting laser light source 33 is in the preparation phase, and so as to turn on the laser status indicator 23b on the operation panel 23 thus to indicate that the exciting laser light source 33 is ready for immediate emission, once the monitor sensor 35 outputs the turn-on enable signal.

Further, the exciting light source drive/control circuit 52 turns on the exciting laser light source 33 when an exciting light turn-on signal is input from the system controller 70 and the timing controller 71, to thereby emit the exciting light to the light guide, and controls the system controller 70 so as to turn on the laser output indicator 23c on the operation panel 23.

In the foregoing fluorescence endoscope system, the buttons on the operation panel 23 may be set to switch the observation modes so as to select one of a normal observation mode of observing the body cavity wall through a color image, a fluorescence observation mode of observing a fluorescent image on the body cavity wall, and a special observation mode of observing a special observation image formed based on the color image and the fluorescent image.

In the normal observation mode, the system controller 70 controls the second motor driver 54 through the timing controller 71 such that the window 37a of the rotary shutter 37 corresponds with the optical path of the white light, and turns on the white light source 30 via the lamp power source 51. Then the white light passes through the window 37a of the rotary shutter 37 and the dichroic mirror 36, and is converged by the condenser lens 32 to be incident upon the light guide 16. The white light transmitted through the light guide 16 illuminates an internal portion of the body cavity through the distributor lens 11. Accordingly, a color image of the body cavity wall is formed on the imaging device 13, via the objective lens 12.

The imaging device control/drive circuit 56 drives the imaging device 13 in synchronization with the timing signal output by the timing controller 71. The image signal from the imaging device 13 is sequentially stored in the RGB memory 58 through the first stage signal processor 57, and processed by the second stage signal processor 59, so that the color image of the body cavity wall is displayed on the monitor 60.

In the fluorescence observation mode, the system controller 70 turns off the white light source 30 through the lamp power source 51, and causes the exciting light source drive/control circuit 52 to open the exciting light shutter 34 under a predetermined condition to be described later, thus to turn on the exciting laser light source 33. The exciting light is reflected by the dichroic mirror 36, thus to be incident upon the light guide 16 through the condenser lens 32. The exciting light transmitted through the light guide 16 illuminates the body cavity wall through the distributor lens 11 to excite the organism tissue thus to induce fluorescence. Accordingly, a fluorescent image of the body cavity wall is formed on the imaging device 13, via the objective lens 12, The imaging device control/drive circuit 56 drives the imaging device 13 in synchronization with the timing signal output by the timing controller 71. The image signal from the imaging device 13 is sequentially stored in the RGB memory 58 through the first stage signal processor 57, and processed by the second stage signal processor 59, so that the fluorescent image of the body cavity wall is displayed on the monitor 60.

Now, in the special observation mode, the system controller 70 controls the second motor driver 54 through the timing controller 71 so as to rotate the rotary shutter 37, and turns on the white light source 30 through the lamp power source 51. The white light is transmitted only when the window 37a of the rotary shutter 37 is at a position corresponding to the optical path, and passes through the dichroic mirror 36 and the condenser lens 32 to be thereby converged, and then enters the light guide 16. The system controller 70 controls the exciting light source drive/control circuit 52 so as to open the exciting light shutter 34 under a predetermined condition to be described later, and turns on the exciting laser light source 33 only in a period that the white light is blocked by the rotary shutter 37, in synchronization with the timing signal from the timing controller 71. The exciting light is reflected by the dichroic mirror 36 to be intermittently incident upon the light guide 16 through the condenser lens 32. Thus, the white light and the exciting light are alternately incident upon the light guide 16, so that the body cavity wall is alternately irradiated with the white light and the exciting light. Accordingly, the color image and the fluorescent image of the body cavity wall are alternately formed on the imaging device 13, through the objective lens 12.

The imaging device control/drive circuit 56 drives the imaging device 13 in synchronization with the timing signal output by the timing controller 71. The first stage signal processor 57 alternately receives the color image signal acquired when the body cavity wall is irradiated with the white light and the fluorescent image signal acquired when the body cavity wall is irradiated with the exciting light and sequentially stores those images in the RGB memory 58. The second stage signal processor 59 compares the color image signal and the fluorescent image signal each time a pair of the color image signal and the fluorescent image signal is received, so as to identify a pixel in which the ratio of the luminance of the fluorescent image signal with respect to that of the color image signal is lower than a predetermined value as representing a lesioned part, and generates an affected part image signal which displays such pixel in red, for example. The second stage signal processor 59 then superposes the affected part image signal on the color image signal, to thereby sequentially generate special observation image data for displaying the body cavity image illuminated by the visible light, including the lesioned part superposed thereon in red, and outputs such data to the monitor 60, The monitor 60 displays the special observation image of the body cavity in which the lesioned part is displayed in red, based on the special observation image data that has been input thereto.

Hereunder, the processing operation performed by the system controller 70 for controlling the exciting laser light source 33 of the electronic endoscope system, configured as above according to this embodiment, will be described referring to the flowcharts shown in FIGS. 5 to 8. For the sake of explicitness of the description, the following process represents the case of executing the fluorescence observation mode.

Figure 5:
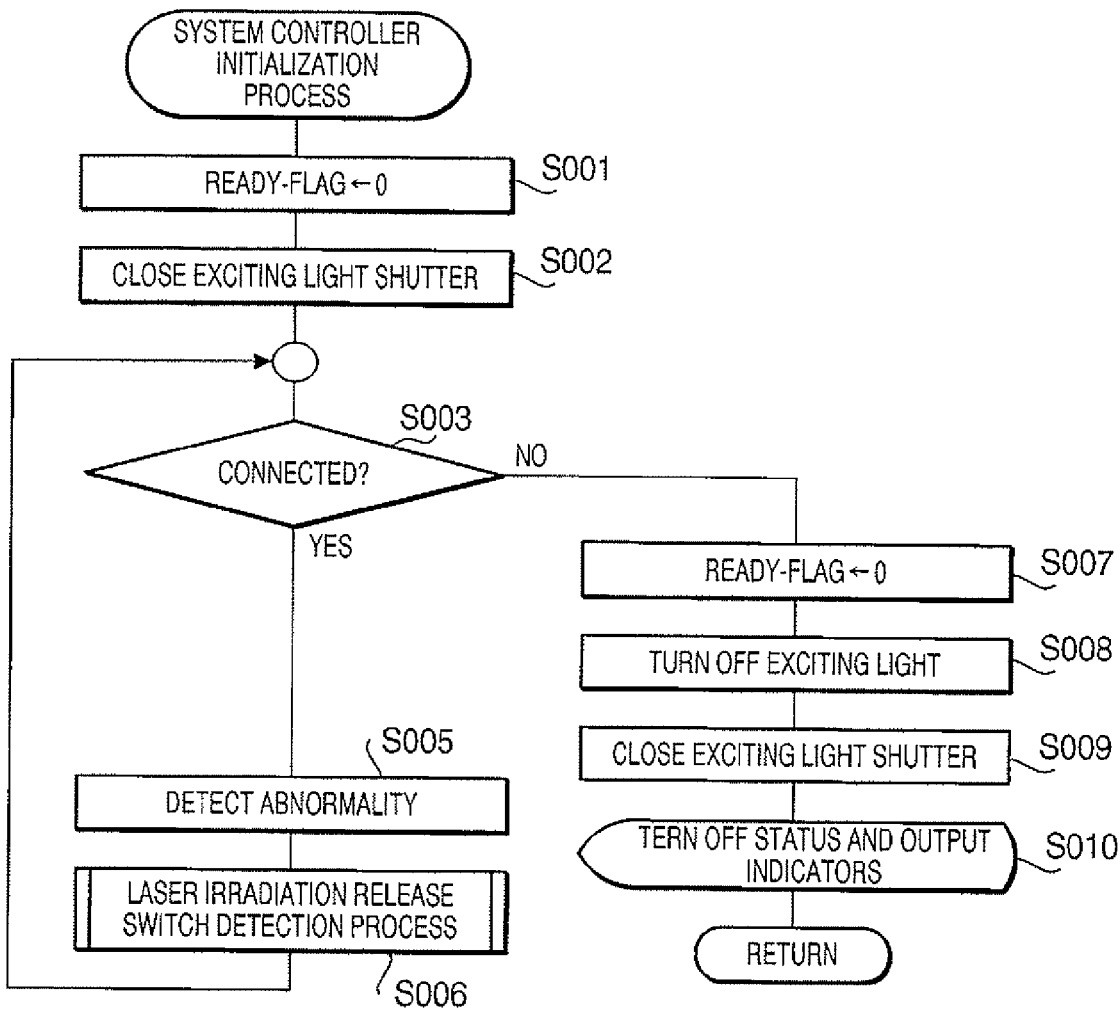
FIG. 5 is a flowchart showing an initialization process of a system controller in the light source processing apparatus shown in FIG. 1.
Figure 6:
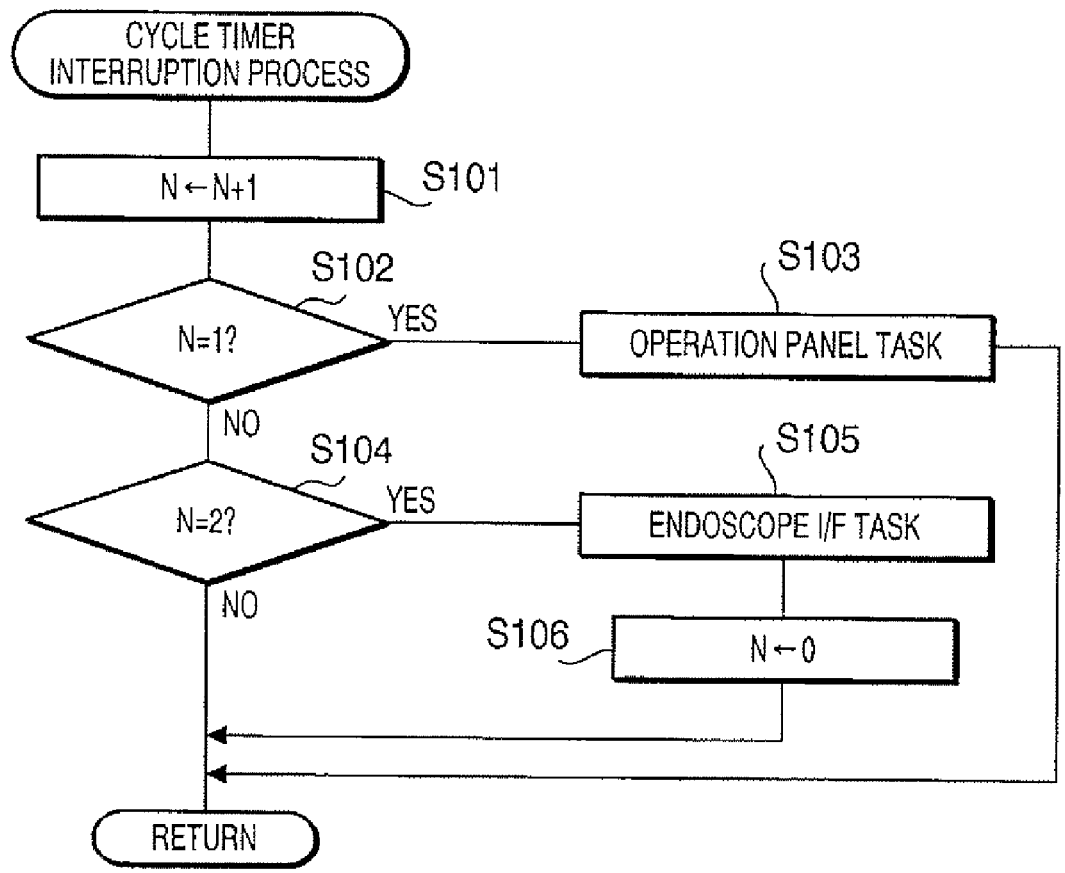
FIG. 6 is a flowchart showing a cycle timer interrupt process of the system controller in the light source processing apparatus shown in FIG. 1.

When a main switch (not shown) of the light source processing apparatus 20 is turned on to supply the power, the main process (not shown) of the system controller 70 is activated, so that an initialization process of the system controller shown in FIG. 5 is called up. Also, a cycle timer interrupt process shown in FIG. 6 is repeatedly executed so as to interrupt the process at a predetermined timing.

In the initialization process of the system controller, the system controller 70 resets the READY-FLAG; indicating a state of the exciting laser light source 33, to 0 (S001). The flag becomes 1 when the exciting laser light source 33 is ready for immediate emission, and is set to 0 in other occasions.

Then the system controller 70 controls the solenoid 34a through the exciting light source drive/control circuit 52 so as to close the exciting light shutter 34 (S002), and detects whether the electronic endoscope 10 is connected to the light source processing apparatus 20 at S003. The system controller 70 detects, once the electronic endoscope 10 is inserted in a socket (not shown) and an electrical connector (not shown) is connected to the socket which is not shown, a change in electrical state (impedance, potential and so on) of the input terminal of the electrical socket, thereby detecting that the endoscope is connected.

When it is decided that the electronic endoscope 10 is connected (Y at S003), the system controller 70 detects abnormality in the exciting laser light source 33 (S005). At this step, abnormality in temperature and current of the laser light source 33 is examined, and if any abnormality is detected the process is deviated from the initialization process of FIG. 5, and an error process (not shown) is executed.

Figure 7:
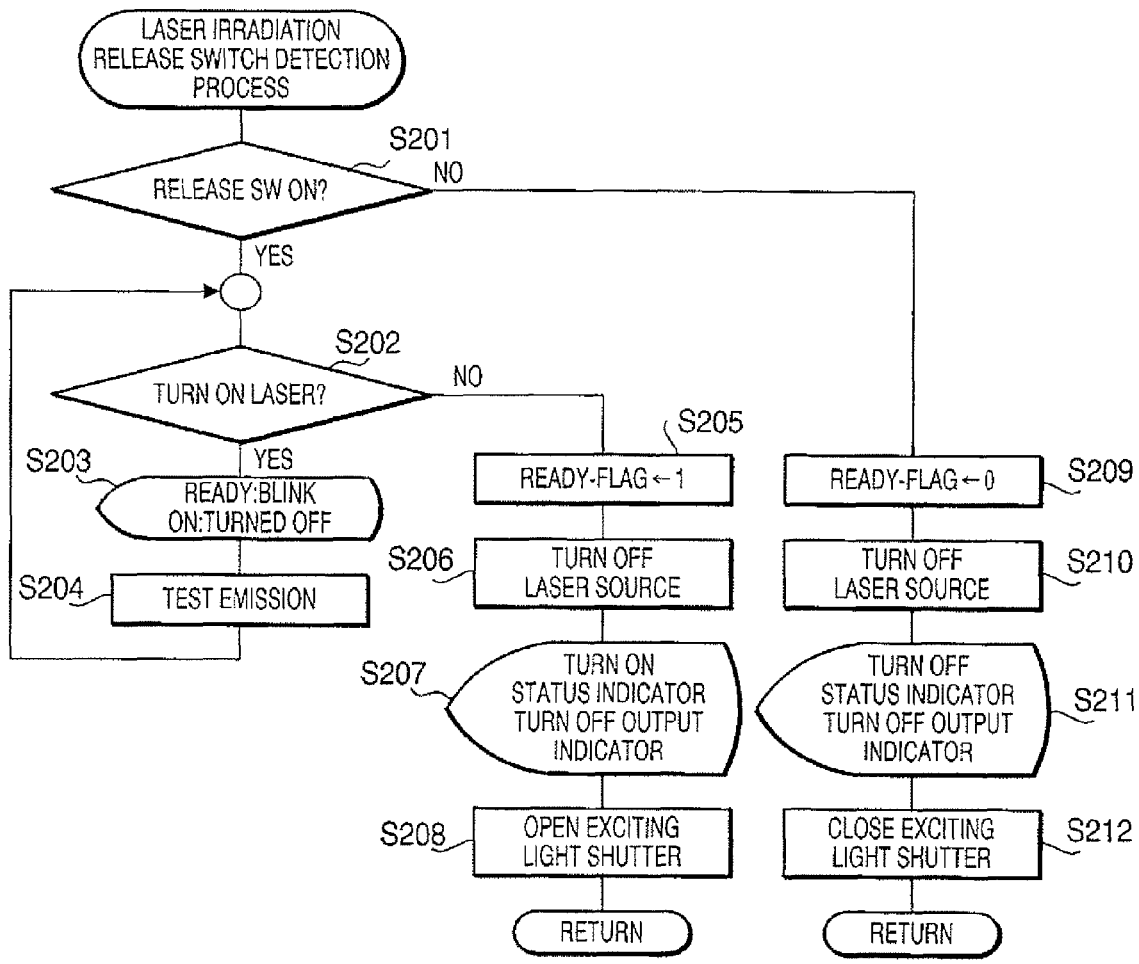
FIG. 7 is a flowchart showing a laser irradiation release switch detection process of the system controller in the light source processing apparatus shown in FIG. 1.

In the case where no abnormality is detected in the exciting laser light source 33, the system controller 70 executes a laser irradiation release switch detection process shown in FIG. 7 (S006). Details of this process will be subsequently described.

On the other hand, when it is decided that the electronic endoscope 10 is not connected to the light source processing apparatus 20 (N at S003), the system controller 70 resets the READY-FLAG to 0 (S007), turns off the exciting laser light source 33 if it is on (S008), and controls the solenoid 34a through the exciting light source drive/control circuit 52 so as to close the exciting light shutter 34 (S009) and to turn off both the laser status indicator 23b and the laser output indicator 23c (S010), and then returns the process to the main process, which is not shown.

When the cycle timer interrupt process shown in FIG. 6 is executed, the system controller 70 increments the task counter N (S101), and confirms the task counter value N at S102 and S104. When the task counter N is 1 (Y at S102), the system controller 70 executes an operation panel task process (S103), and returns the process to the main process which is not shown. When the task counter N is 2 (Y at S104), the system controller 70 executes an endoscope interface (hereinafter, I/F) process shown in FIG. 8 (S105), resets the task counter N to 0 (S106), and returns the process to the main process, which is not shown.

When the laser irradiation release switch detection process is executed at S006 in FIG. 5, the system controller 70 firstly decides, as shown in FIG. 7, whether the laser irradiation release switch 22 is on, through the exciting light source drive/control circuit 52 (S201). For the exciting laser light source 33 to be turned on, it is necessary that the laser irradiation release switch 22 is on. In the case where the laser irradiation release switch 22 is on (Y at S201), the system controller 70 decides whether the exciting laser light source 33 is on (S202), and causes the laser status indicator 23*b* to blink in preparation for the emission if the exciting laser light source 33 is not yet turned on, turns off the laser output indicator 23*c* (S203), and performs test emission of the exciting laser light source 33 through the exciting light source drive/control circuit 52 (S204). To execute the test emission, a current is supplied to the exciting laser light source 33 for a short period of time. Since the exciting light shutter 34 remains closed during the test emission, the exciting light is kept from being emitted outward from the distal tip portion of the endoscope.

The exciting light source drive/control circuit 52 repeats the test emission until the exciting laser light source 33 is stably turned on and the monitor sensor 35 outputs the turn-on enable signal (until Y is selected at S202), and once S202 turns out to be Y the system controller 70 decides that the exciting laser light source 33 has been through the preparation phase, sets the READY-FLAG to 1 (S205), turns off the exciting laser light source 33 (S206), turns on the laser status indicator 23*b* and turns off the laser output indicator 23*c* (S207), and then controls the solenoid 34*a* through the exciting light source drive/control circuit 52 so as to open the exciting light shutter 34 (S208) and returns the process to S003 in FIG. 5.

When the laser irradiation release switch 22 is off (N at S201), the system controller 70 resets the READY-FLAG to 0 (S209), turns off the exciting laser light source 33 (S210), turns off both the laser status indicator 23*b* and the laser output indicator 23*c* (S211), and controls the solenoid 34*a* so as to close the exciting light shutter 34 (S212), after which the process is returned to the initialization process of the system controller shown in FIG. 5.

Figure 8:
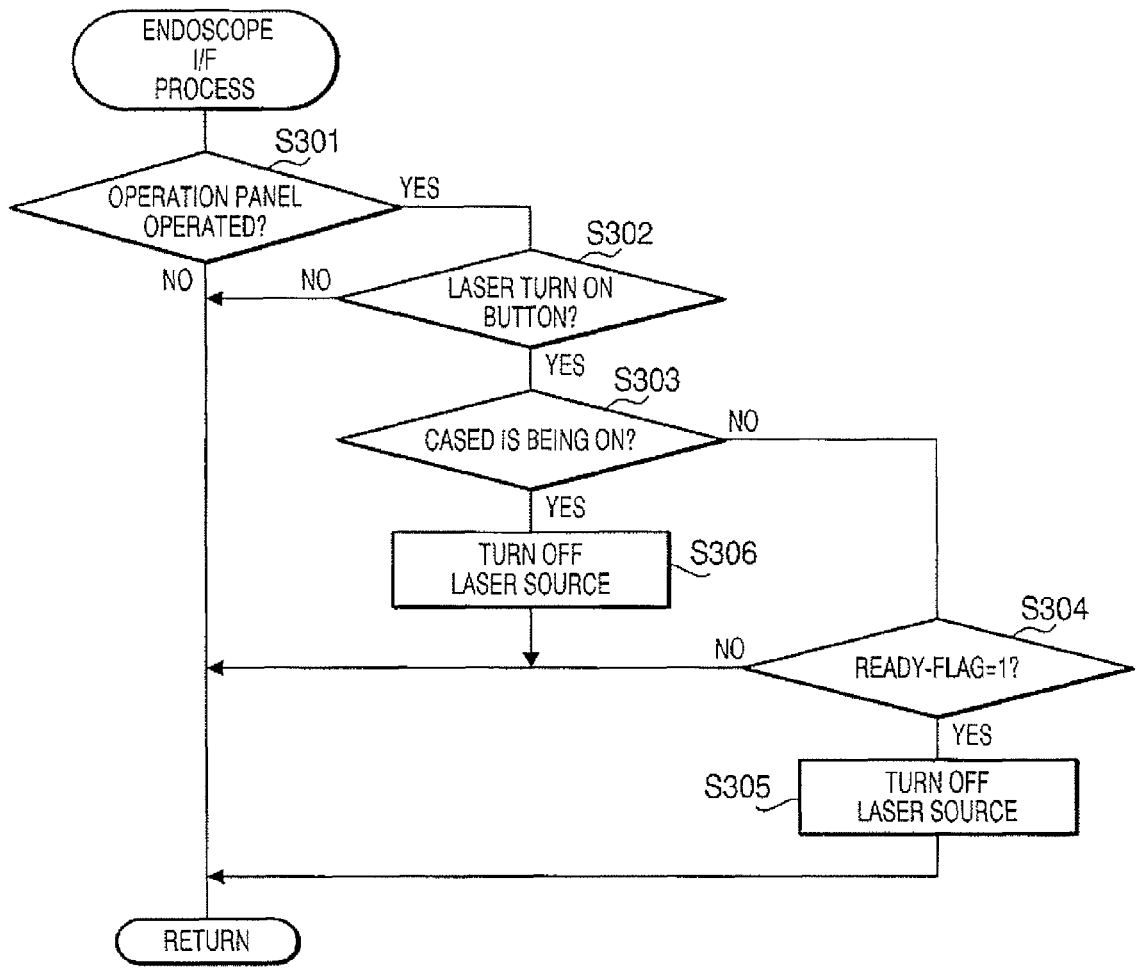
FIG. 8 is a flowchart showing an endoscope I/F task process of the light source processing apparatus shown in FIG. 1.

When the endoscope I/F process is executed at S105 in FIG. 6, the system controller 70 decides, as shown in FIG. 8, whether any of the buttons on the operation panel 23 has been manipulated (S301). If no button has been manipulated, the process is directly returned to the cycle timer interrupt process in FIG. 6. In the case where any of the buttons on the operation panel has been manipulated (Y at S301), the system controller 70 decides whether it is the laser turn-on button 23*a* that has been manipulated (S302), and in the negative case the process is directly returned to the cycle timer interrupt process in FIG. 6.

In the case where it is the laser turn-on button 23*a* that has been manipulated (Y at S302), the system controller 70 then decides whether the exciting laser light source 33 is on (S303). In the negative case (N at S303), the system controller 70 decides whether the READY-FLAG value is 1 (S304), and if affirmative turns on the exciting laser light source 33 (S305), and then returns the process to the cycle timer interrupt process in FIG. 6. If the laser exciting laser light source 33 is on when the laser turn-on button 23*a* is manipulated (Y at S303), the system controller 70 turns off the exciting laser light source 33 (S306), and returns the process to the cycle timer interrupt process in FIG. 6.

Through the foregoing steps, when the electronic endoscope 10 is connected to the light source processing apparatus 20, the laser irradiation release switch 22 is turned on, and the exciting laser light source 33 becomes ready for immediate emission and the exciting light shutter 34 is opened, and when the exciting light turn-on signal is input under such state the exciting laser light source 33 is turned on, so that the exciting light is made incident upon the light guide 16, and then transmitted through the insertion tube 10*a* of the electronic endoscope thus to be emitted onto the body cavity wall opposing the distal tip portion of the insertion tube 10*a*.

The operator can notice, in view of the laser status indicator 23*b* on the operation panel 23, that the laser light source cannot be turned on yet when the laser status indicator 23*b* is off, that the laser light source is in the preparation phase when the laser status indicator 23*b* is blinking, and that the laser light source can be immediately turned on when the laser status indicator 23*b* is on, and is hence exempted from taking the trouble of repeatedly pressing the laser turn-on button during the preparation phase, thus being released from troublesome operation.

Since the process shown in FIG. 8 is arranged based on the fluorescence observation mode, the exciting light turn-on signal is generated when the READY-FLAG is set to 1 and the laser turn-on button 23*a* is pressed while the exciting laser light source 33 is off. In the special observation mode, the exciting light source drive/control circuit 52 generates the exciting light turn-on signal while the white light is blocked by the rotary shutter 37, according to the timing signal output by the timing controller 71.

Although the laser turn-on button is located on the operation panel of the light source processing apparatus 20 in the foregoing embodiment, the laser turn-on button may be located on the operating unit 10*b* of the electronic endoscope 10. Also, instead of or in addition to providing the laser status indicator on the operation panel 23, the monitor 60 may be set to display, in a section thereof, to the effect that the laser light source is in the preparation phase or ready for immediate emission.

The light source apparatus for an endoscope according to the embodiment described above automatically executes test emission of the exciting laser light source once the power is turned on, and indicates, when the exciting laser light source becomes ready for immediate emission, to such effect. Accordingly, the operator can be notified that the exciting laser light source is ready to be used, without the need to repeatedly press the turn-on button. Also, since the shutter is closed during the period of the test emission, the laser beam can be prevented from being unduly emitted toward outside.

The present disclosure relates to the subject matter contained in Japanese Patent Application No. 2005-311685, filed on Oct. 26, 2005, which is expressly incorporated herein by reference in its entirety.

What is claimed is:

1. A light source apparatus for an endoscope, designed to make an exciting light that excites an organism tissue to thereby induce fluorescence incident upon a light guide disposed through a portion of the endoscope to be inserted into a body cavity, comprising:

an exciting laser light source that emits the exciting light;

a monitor sensor that monitors an output of the exciting laser light source and outputs a turn-on enable signal when the exciting laser light source is ready to stably emit a beam;

an indicator that indicates whether the exciting laser light source is ready for immediate emission;

a shutter mechanism that opens and closes an optical path of the exciting light; an optical system that makes the exciting light that has passed the shutter mechanism incident upon a proximal face of the light guide; and a controller that controls the exciting laser light source; wherein the controller intermittently turns on the exciting laser light source for testing and controls the shutter mechanism so as to close the optical path of the exciting light, during a period after laser irradiation is permitted until the monitor sensor outputs the turn-on enable signal, the controller controlling the shutter mechanism so as to open the optical path of the exciting light and controls the indicator so as to indicate to the effect that the exciting laser light source is ready for immediate emission, when the monitor sensor outputs the turn-on enable signal, and the controller turning on the exciting laser light source when an exciting light turn-on signal is input, thereby making the exciting light incident upon the light guide.

2. The light source apparatus for an endoscope according to claim 1, wherein the controller controls the indicator so as to indicate to the effect that the exciting laser light source is in a preparation phase, during a period after laser irradiation is permitted until the monitor sensor outputs the turn-on enable signal.

* * * * *